United States Patent [19]
Marici

[11] 3,931,822
[45] Jan. 13, 1976

[54] AUTOMATIC ALTERNATING CUFF ENDO TRACHEAL TUBE INFLATOR

[76] Inventor: Frank N. Marici, 2 Mineola Ave., Roslyn, N.Y. 11576

[22] Filed: Feb. 26, 1974

[21] Appl. No.: 446,057

[52] U.S. Cl. .......................... 128/351; 128/349 BV
[51] Int. Cl.² ....................................... A61M 16/00
[58] Field of Search.......... 128/208, 349 B, 349 BV, 128/351

[56] References Cited
UNITED STATES PATENTS

| | | | |
|---|---|---|---|
| 3,529,596 | 9/1968 | Garner | 128/351 X |
| 3,794,026 | 2/1974 | Jacobs | 128/351 X |

OTHER PUBLICATIONS

Crosby, W. M., "Automatic Intermittent Inflation of Tracheostomy-Tube Cuff", In the Lancet, No. 7358, Vol. II for 1964, p. 509, Sept. 5, 1964.
Salpekar, P. D., "New Apparatus for Chest Units", IN Brit. Med. J., 1966, Vol. 1, 296, Jan. 29, 1966.

Primary Examiner—Channing L. Pace
Attorney, Agent, or Firm—Pollock, Philpitt & Vande Sande

[57] ABSTRACT

A multi-cuff endo-tracheal tube which minimizes the irritation to the trachea by alternately inflating one or the other of two cuffs. A short period of time after one cuff is inflated the previously inflated cuff is deflated. This removes the possible source of irritation on the trachea at the point of contact with the second cuff. After the first cuff has been in operation for a predetermined period of time, the second cuff is inflated and after another short interval, the first cuff is deflated. A control system alternately and sequentially inflates and deflates the cuffs in the proper sequence, automatically. The control system is fail-safe in that, in the event of cuff rupture, overpressurization, or electrical failure, one or the other of the cuffs remains inflated to seal the endo-tracheal tube and the control system alerts attendant personnel.

11 Claims, 4 Drawing Figures

AUTOMATIC ALTERNATING CUFF ENDO TRACHEAL TUBE INFLATOR

FIELD OF THE INVENTION

This invention relates to medical and surgical devices and more particularly to a sealing device for use with a specialized endo-tracheal tube.

BACKGROUND OF THE INVENTION

For some time there has existed a need for extended controlled ventilation in patients with severe lung ailments. In one procedure which has been devised to meet this need, endo-tracheal intubation has been devised which comprises inserting a tube through the upper airways (trachea) of the patient. The tube is then used to connect the respiratory apparatus of the patient to a mechanical ventilating device or respirator.

For a number of reasons it is usually necessary to form a seal between the endo-tracheal tube and the inside of the tracheal wall of the patient. The extended controlled ventilation requires intermittent pressurization of the patient's respiratory apparatus, and the seal is necessary if a pressure above atmospheric is to be maintained within the patient's respiratory system. To obtain this seal, the endo-tracheal tube is provided with a cuff which is capable of being inflated once in place. Since the patient may require the use of the endo-tracheal tube for several days or weeks, it is common for the trachea to become irritated at the point where the cuff engages the tracheal wall, leading to necrosis, scarring, and possibly stenosis, (see *Intratracheal Cuff: Performance Characteristics*, By Carroll, Hedden and Safar, in Anesthesiology, September 1969, pages 275-281).

At least some of the causes of the difficulties with prior art cuffs can be traced to the fact that the pressure of the cuff, acting against the trachea, can be great enough to cut off the blood circulation in the trachea thus causing damage. The prior art has recognized that, in the period between inhalation and exhalation, the pressure in the cuff can be decreased to allow blood circulation to flow in the tracheal walls, (see, for instance, U.S. Pat. No. 3,481,339).

The prior art (see for example, U.S. Pat. No. 3,481,339) has also suggested that tubes with successive cuffs could be used, so that successive compression can be carried out with different parts or portions corresponding to each cuff. However, while the prior art teaches a cuff which is capable of automatically decompressing between inhalation and exhalation, U.S. Pat. No. 3,481,339 states that successive cuffs were disadvantageous since the assistance of an expert was required.

SUMMARY OF THE INVENTION

The present invention comprises an automatic alternating cuff endo-tracheal tube. In the illustrated embodiment, two cuffs are provided which are inflated and deflated sequentially for short periods of time so that the tracheal mucosa can recover during the periods of time when the adjacent cuff is deflated. Furthermore, the pressure in an inflated cuff varies continuously during the breathing cycle in accordance with the variation in pressure supplied to the trachea by the tube connected to a respirator. In particular, the cuff pressure is just slightly higher than the pressure in the trachea to maintain the seal and minimize the irritation.

The sequence of operation is to inflate the second cuff, before the first cuff is deflated and maintain both inflated for a short, predetermined period of time, the first cuff may be then inflated and both cuffs maintained inflated for a short predetermined period of time, after which the second cuff can be deflated. In this manner, a positive seal is maintained at all times.

To control the inflation and deflation of the cuffs sequentially, the control system must provide the following functions:

1. The system must inflate and deflate the cuffs in the proper sequence and with the proper time overlap as described above.

2. The system must be simple to operate so as not to require a skilled expert to be standing by at all times when the system is in operation. It is expected that during extended periods of time, only semi-skilled personnel will be available to monitor the patient's progress.

3. The control system must be fail-safe. The tube must remain sealed at all times even subsequent to a malfunction and, in the case of a malfunction, the attendant personnel must be alerted. The control system is capable of responding to the following malfunctions: cuff rupture, overpressurization of the patient due to accumulation of mucus causing atelectasis and electrical failure in the control system.

BRIEF DESCRIPTION OF THE DRAWINGS

As an aid to describing the illustrated embodiment of the invention, reference will be made to the several figures of drawings in which like reference characters refer to identical apparatus and in which.

DETAILED DESCRIPTION OF THE DRAWINGS

Figure 1:
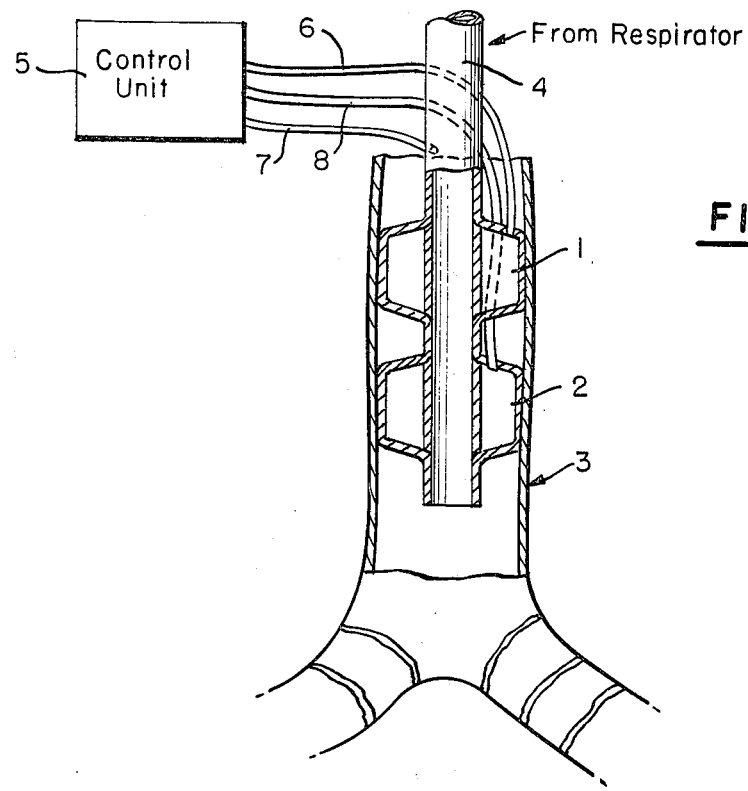
FIG. 1 is a schematic showing of the alternating cuff endo-tracheal tube inserted in a trachea.

FIG. 1 illustrates the alternating cuff endo-tracheal tube in place in the trachea. In particular, the endo-tracheal tube 4 is inserted in the trachea 3. A conventional respirator supplies air to the endo-tracheal tube 4 which is then supplied to the trachea. To effect a seal between the trachea and atmospheric pressure, a pair of cuffs, 1 and 2, surrounds the tube at two different locations. Each of the cuffs 1 and 2 is inflatable and therefore air-tight. A control unit 5 senses and controls the pressure in cuffs 1 and 2 through communicating lines 6 and 8, respectively. The pressure in the endo-tracheal tube 4 is sensed by the control unit 5 via pressure line 7.

Figure 2:
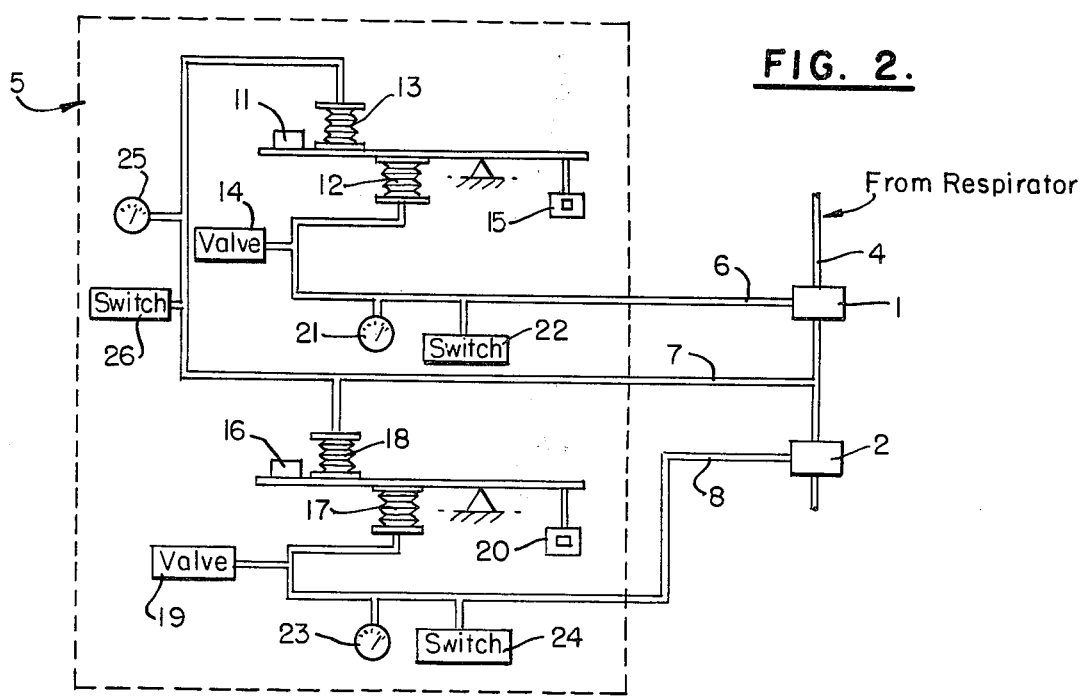
FIG. 2 is a schematic diagram illustrating the pneumatic components of the system and their interconnection.

FIG. 2 shows the pneumatic portion of the control unit 5 in its relation to the endo-tracheal tube 4 and the cuffs 1 and 2. The control unit includes a pressure gauge 25 which is responsive to the pressure in endo-tracheal tube 4. In addition, pressure sensing gauges 21 and 23 are provided to sense, respectively, the pressure in cuffs 1 and 2 via the communicating lines 6 and 8. Pressure-actuated electrical switches 22, 24, and 26 each are provided to open or close an electric circuit in response to the pressure in cuff 1, cuff 2, or tube 4, respectively. The remaining portions of the control unit 5 include a pneumatic sensing and controlling device for each of cuffs 1 and 2. This portion of the control unit 5 is shown in more detail in FIG. 3 for that pneumatic control sensing unit associated with cuff 1.

Figure 3:
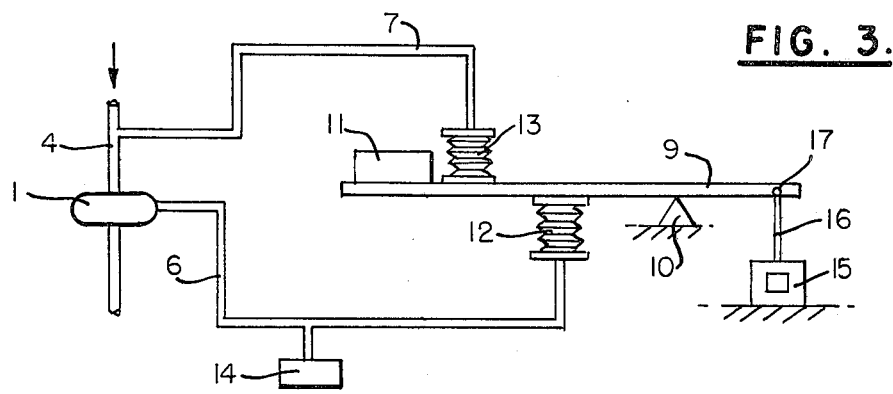
FIG. 3 is a detail showing of a portion of the pneumatic components of the system related to one of the two cuff.

FIG. 3 repeats the showing of endo-tracheal tube 4 and cuff 1. These are, respectively, connected to a bellows or transducers (hereinafter the term "bellows" will be used even though such devices, are transducers) 13 and 12 through pneumatic lines 7 and 6, respectively. The upper end of bellows 12 and the lower end of bellows 13 are connected to a common lever arm 9 which pivots about a pivot point 10. A weight 11 is placed on lever arm 9 to tend to depress the bellows 12. A solenoid 15, acting through its arm 16, which is connected to the lever arm 9 and pin 17, is capable of rotating lever arm 9 about its pivot point 10. A unidirectional valve 14 is connected to line 6 communicating with cuff 1 and the bellows 12. The valve 14 allows atmospheric air to enter the communicating line 6 and through the line 6 to the cuff 1 and the bellows 12 when the bellows 12 is expanded. However, when the bellows 12 contracts, valve 14 prevents air leakage to the atmosphere and thus the pressure in cuff 1 and bellows 12 rises.

Although not illustrated in FIG. 3, a similar unit to the one shown in FIG. 3 is associated with cuff 2. This is shown schematically in FIG. 2.

In operation, the cuff 1, shown in FIG. 3, is inflated by compression of bellows 12. When the solenoid 15 is energized, arm 16 retracts causing the lever arm 9 to pivot in a clockwise direction about pivot point 10 to expand the bellows 12 and deflate the cuff. When the solenoid 15 is deenergized, lever arm 9 rotates in a counterclockwise direction, allowing weight 11 to compress the bellows 12. This increase in pressure is transmitted to the cuff 1, thereby inflating it. Bellows unit 13, communicating with the pressure in tracheal tube 4, expands and contracts in response to the pressure variations in the tracheal tube. As the pressure in the tracheal tube 4 increases, the bellows 13 expands and, correspondingly, as the pressure in tracheal tube 4 decreases, the bellows 13 contracts.

Assuming cuff 1 is to be inflated, solenoid 15 is deenergized allowing the weight 11 to compress the bellows 12. The steady downward force on the lever arm 9 caused by the weight 11 compresses the bellows 12 to inflate the cuff 1. As the respirator, which supplies air to the tracheal tube 4, forces air into the tube, the tracheal pressure increases. This causes bellows unit 13 to expand to increase the force exerted on the bellows unit 12. Thus, the pressure in cuff 1 will increase to a value greater than the steady pressure caused by the weight 11. If the bellows 12 is positioned directly beneath the bellows 13, the cuff pressure will theoretically equal the pressure caused by the weight plus the tracheal pressure. By varying the weight 11, one may chose any initial pressure desired. Bellows 13 is not necessarily located directly above bellows 12. If it is positioned farther from pivot point 10 of the lever arm 9 than is bellows 12, a mechanical advantage results and a greater increase in cuff pressure will result from a given increase in tracheal pressure. This may be desirable to counteract the friction in the moving parts, pressure drops in lines, and back pressure caused by the stiffness of the cuff. With a correct choice of initial pressure and mechanical advantage in the lever arm it is possible to maintain just enough pressure in the cuff to maintain an effective seal throughout the entire breathing cycle and, at the same time, not overpressurize the cuffs so as to irritate the mucosa. When it is desired to deflate cuff 1, the solenoid 15 is energized. This causes clockwise rotation of lever arm 9 about pivot 10, raising weight 11, expanding bellows 12, and deflating the cuff 1.

It should be noted, at this point, that electrical energy is not required to inflate either cuff 1 or cuff 2. The energy for inflation of the cuffs is provided by the respirator. As the respirator increases the pressure in the endo-tracheal tube 4, this causes the associated bellows unit (i.e. either 13 or 18, see FIG. 2) to expand to cause a corresponding contraction of bellows unit 12 or 17. The contraction of the bellows units 12 or 17 increases the pressure in the corresponding one of the cuffs 1 or 2. Electrical energization of the solenoid, either solenoid 15 or solenoid 20, merely provides for deflation of the respective cuff.

Figure 4:
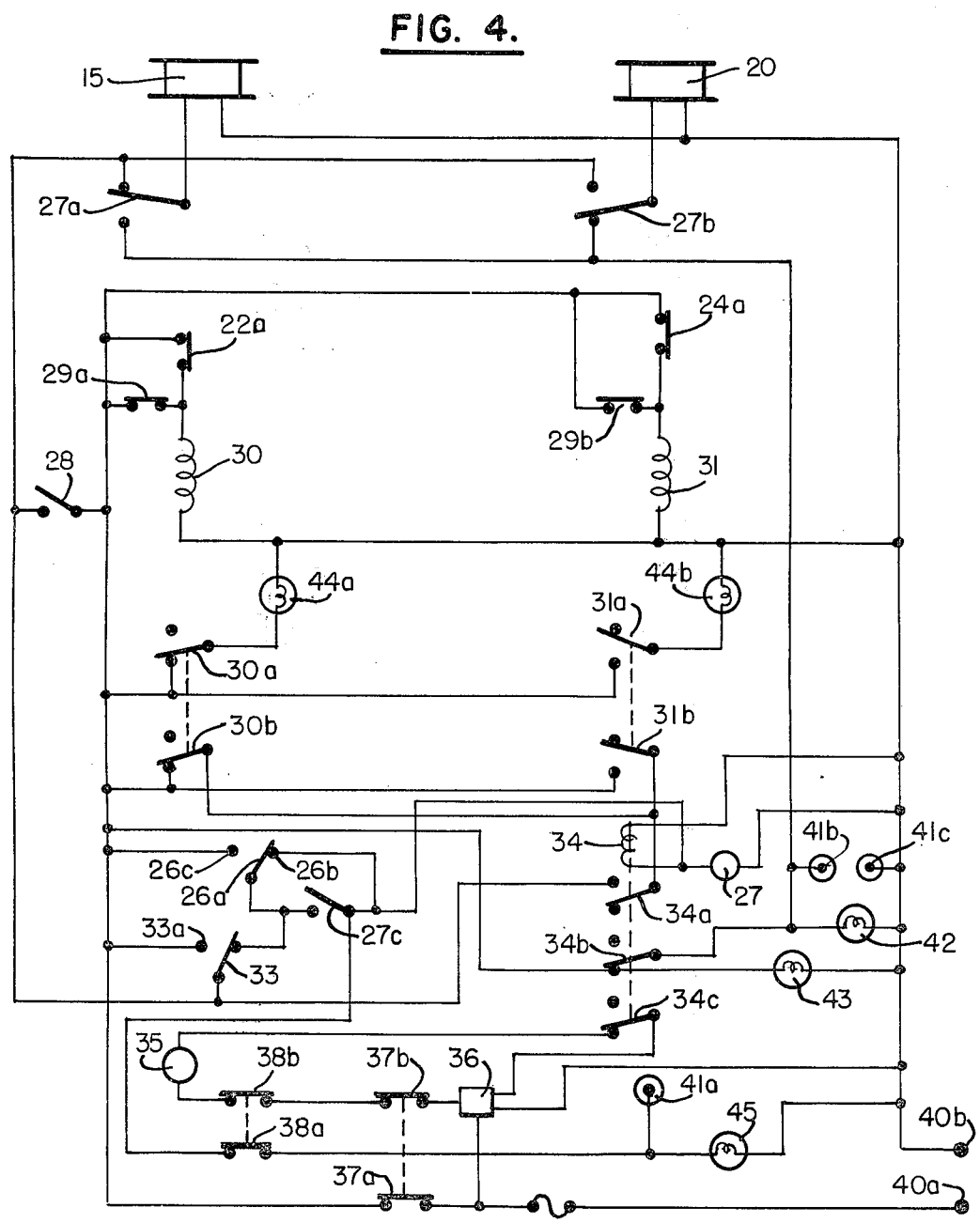
FIG. 4 is an electrical schematic showing the electrical portions of the control system.

FIG. 4 shows the electrical portion of control unit 5. As noted above, electrical energy is not required for the inflation of either cuff 1 or cuff 2. However, electrical energy is required to cycle the cuffs, that is, to cause the selective deflation of one or the other of the cuffs in the proper sequence. Furthermore, the electrical portion of control unit 5 can respond to a variety of faults in a fail-safe manner including cuff rupture, overpressurization of the patient, or electrical failure. In any of these cases, appropriate warning indicators are energized to alert attendant personnel. Furthermore, indicating lights are energized to indicate the condition of the apparatus.

FIG. 4 shows the solenoids 15 and 20 which are respectively energized over switches 27a and 27b. These switches are controlled by timer 27, which also controls timer switch 27c. These switches are so arranged that during normal operation, one switch, for instance 27a, is closed for a predetermined period of time, such as 20 minutes. During that same interval of time, switches 27b and 27c are open. For purposes of this description, switches 27a and 27b are considered open when they are in their lower position and closed when in their upper position. Switch 27c is closed when in its lower position. After the timer 27 has timed out the predetermined period of time, the associated closed switch opens and switch 27c closes for a short period of time, such as 30 seconds. At the expiration of this short period of time, switch 27c again opens and the other switch, for instance, 27b, closes.

Relays 30, 31 and 34, respectively, control contacts 30a, 30b; 31a, 31b; and 34a, 34b and 34c. When the respective relay is energized the contacts are raised and when the relay is deenergized the contacts correspondingly fall. Relays 30 and 31 can be energized respectively via either closed switches 22a, 29a and 24a, 29b, respectively. The switches 22a and 24a are the contacts of the pressure switches 22 and 24 shown in FIG. 2. When the pressure in lines 6 or 8, corresponding to the pressure in cuffs 1 or 2, rises sufficiently to indicate that the cuff is inflated, then the switches 22a or 24a are closed. Correspondingly, when the cuffs are deflated, these switches are opened.

In the event of a slow leak in the air supply line to either cuff 1 or 2, the decrease in pressure may be so slight as not to trip the respective pressure switch 22 or 24. However, as the lever arm cycles in response to pressure variations in a tracheal tube 4, slow leak either in a cuff or in the air supply line leading from a bellows 12 or 17 to the associated cuff will cause the corresponding lever arm to rotate further in the counterclockwise direction because of the lower counter pressure. A limit switch (not shown in FIG. 2) is positioned so as to be closed in response to the greater amount of travel of such lever. Limit switch 29a in FIG. 4 is associated with cuff 1 and limit switch 29b is associated with cuff 2. These limit switches are normally open and become closed in response to the detection of lever arm travel which exceeds a predetermined limit.

Indicator lights 44a and 44b, when energized, indicate that the respective cuff, cuff 1 or cuff 2, is inflated.

Pressure switch 26 operates to one of two positions depending upon whether or not the pressure in the tracheal tube 4 exceeds a predetermined limit corresponding to overpressurizing the patient. The transfer contact 26a (in FIG. 4) is thus operated to the right, making contact with 26b when the pressure is normal, and is operated to the left, to make contact with 26c, when the pressure increases above the threshold.

Indicator light 42 is a red warning light, and is energized at any time other that an apparatus malfunction occurs. Indicator light 43 is energized when power is applied to the system, and green indicator light 45 is energized when the system is operating properly.

An audible alarm 35 is provided which is energized when the system is not operating properly. The alarm is energized via a nickel cadmium battery 36 which has an associated recharger which is shown connected to the power lines.

Jacks 41a, 41b and 41c are allowed for convenient connections for remote indication purposes. On-off switches 37a and 37b are provided along with switches 38a and 38b which may be opened by an operator to disable the audible alarm. A reset switch 28 is provided to initiate the operation of the system and deflate switch 33 is provided which, when thrown to its leftmost position, contacting 33a, will cause the cuffs to deflate.

OPERATION

In order to explain the operation of the control system, the functions that are performed in a normal cycle will be explained and this will be followed by a description of the manner in which the apparatus responds to various types of malfunction.

When the system is first energized, both relays 30 and 31 will be energized via the power line through switch 37a and the closed pressure switches 22a and 24a. Relay 34, however, will be deenergized and thus power will be applied through switch 37a, and back contacts of 34b and 27b to energize solenoid 20, thus ensuring that cuff 2 remains deflated. Solenoid 15 is deenergized, but cuff 1 is also deflated since lever arm 9 is initially in its extreme counterclockwise position and bellows 12 is compressed. The power indicator 43 will be energized also over contact 34b. Also, a red warning light 42 will be energized and the audible alarm 35 will be activated. The sounding of the alarm can be discontinued by opening switch 38a and b, if desired. In order to initiate operations, the reset switch 28 is closed. This will energize timer motor 27 and relay 34 through switch 33 and switch 26a in contact with 26b.

Closing the reset switch 28 will also provide a source of power over contact 28 to solenoid 15 to energize solenoid 15. At the same time, however, the picking up of relays 34 opens the energization circuit for solenoid 20 at open contact 34b and thus solenoid 20 will be deenergized to allow inflation of cuff 2. At the same time, the red warning light 42 will be deenergized. As the pressure builds up in cuff 2, pressure switch 24a will open, thus deenergizing relay 31. This will energize indicator 44b over the back contact of relay contact 31a, indicating that cuff 2 is inflated. Energization of relay 34 deenergizes the red indicator 42 and also opens the circuit for the audible alarm 35 at relay contact 34c. If switches 38a and 38b are now closed, the green indicator 45 will be energized indicating normal operation.

In general, normal operation is indicated by relay 34 being energized. This will only occur if one or the other of relays 30 and 31 is deenergized.

After the predetermined sequencing period (such as 20 minutes) has been timed out by motor 27, contact 27a will open to thus deenergize solenoid 15. At this time, solenoid 20 is already deenergized, and thus, in response, both cuffs 1 and 2 will become inflated. At the same time that contact 27a opens, 27c will close. If cuff 1 inflates, pressure switch 22a will open and thus relay 30 will become deenergized. Now both indicators 44a and 44b are energized, indicating that both cuffs are inflated. However, relay 34 remains energized. After a short predetermined period of time (such as 30 seconds), the timer 27 causes switch 27c to open and 27b to close, that is, to assume its upper position. This will cause solenoid 20 to be energized over the back contact of either 30b or 31b and through the front contact of 34a to the closed switch 27b. This will cause cuff 2 to deflate and thus cause switch 24a to close again, energizing relay 31. This will cause indicator 44b to be extinguished, but indicator 44a remains energized, indicating that cuff 1 is still inflated.

In this manner, the control unit cycles cuffs 1 and 2, with cuff 1 inflated for a predetermined period of time (such as 20 minutes), after which both cuffs 1 and 2 are inflated for a short predetermined period of time (such as 30 seconds), after which cuff 1 is deflated and cuff 2 becomes inflated for a similar predetermined period of time (such as 20 minutes). This normal sequence of operation continues as long as no failures are detected.

The actual pressure source to cause the cuffs to become inflated is the respirator, over the apparatus shown in FIG. 2. If, after the machine has been in operation, it is desired to deflate both cuffs 1 and 2, for instance, for repositioning the endo-tracheal tube 4, or for removing it, switch 33 may be operated to its lefthand position to make contact 33a. Since relay 34 is normally energized through switch 33 in its righthand position, actuation of the switch to its lefthand position will cause deenergization of relay 34. This will supply power to the normally open contact for switch 27a or 27b, depending on the condition of the timer 27. This power will cause energization of either solenoid 15 or 20. In addition, when switch 33 makes contact 33a power will be supplied to the normally closed side or either switch 27a or 27b. Thus, the other solenoid will also be energized. This will cause deflation of both cuffs, and at the same time energize red warning indicator 42 and audible alarm 35.

Loss of power in the electrical portion of the control system 5 will cause all relays and solenoids to become deenergized. The audible alarm 35 will be energized, however, by reason of a nickel-cadmium battery 36. At the same time, it should be noted that both cuffs will be inflated, thus protecting the patient in case of electrical power failure.

Another potential failure situation which the control system must handle properly is that of cuff rupture or a rupture of the lines 6 or 8 feeding the cuffs. For purposes of this explanation, it will be assumed that cuff 1 is deflated, that is solenoid 15 is energized, and that solenoid 20 is deenergized and therefore cuff 2 is inflated. This will mean that the timer switches 27a and 27b will be in the position shown in FIG. 4. Pressure switch 22a will be closed and 24a will be open indicating pressure in cuff 2. Relay 30 will be energized through the closed switch 22a, and relay 31 will be deenergized since both the pressure switch 24 is open and the limit switch 29b is open. Relay 34 will be energized, indicating normal operation. At the time cuff 2 ruptures, pressure switch 24a will be closed due to the decrease in pressure. This will energize relay 31. Since relay 34 had been energized over the back contact of 31b, energization of relay 31 removes the energy from relay 34 and it becomes deenergized, energizing the red warning lamp 42 and sounding the audible alarm 35. In addition, the timer motor 27 will stop since it, too, was supplied with energy over the back contact of 31b. The energy for energizing solenoid 15 had been supplied over the same back contact of 31b. When relay 31 was energized, this energy path opened and thus solenoid 15 was deenergized. The deenergization of solenoid 15 allows cuff 1 to become inflated and, at the same time, energy is supplied over back contact 34b to energize solenoid 20 to cause cuff 2 to become deflated if it has not already done so. When cuff 1 inflates, pressure switch 22a opens, thus dropping relay 30. This will cause indicator 44a to become energized over the back contact of 30a. Thus, in response to the rupture of air inflated cuff, the faulty cuff has been deflated and the other cuff inflated. The system indicates a failure mode by sounding the alarm and energizing red indicator 42 so that the attendants may be informed and take proper action. With indicator 44a energized, this indicates that cuff 1 is inflated and therefore the problem lies in cuff 2. In case cuff 1 ruptures, similar operation will ensure that cuff 2 becomes inflated.

A further possible failure mode is a slow leak in one of the cuffs which does not depressurize the system enough to close the associated pressure switch. Instead, one of the lever arms will gradually move lower until it trips either limit switch 29a or 29b. Assume that cuff 2 has been inflated and cuff 1 deflated. This will cause relays 30 and 34 to be energized and relay 31 to be deenergized. If the slow leak is associated with cuff 2, limit switch 29b will close, thus energizing relay 31. When contact 31b moves up, it opens the energization path for relay 34 and thus this relay becomes deenergized. This will activate the red warning lamp 42 and initiate the audible alarm 35. As in the previous example, when relay 31 is energized, it also opens the energy path for energizing solenoid 15 and thus this solenoid becomes deenergized allowing cuff 1 to inflate. At the same time, when relay 34 is deenergized, the back contact at 34b provides an energy supply for energizing solenoid 20, thus causing cuff 2 to deflate. This same action causes the lever arm to move up and opens limit switch 29b. However, pressure switch 29a will close due to the drop in pressure and thus maintain relay 31 energized. As cuff 1 inflates, pressure switch 22a will open, thus deenergizing relay 30 and providing a current path for energizing indicator 44a over the back contact at 30a. At the same time that the relay 34 became deenergized, timer motor 27 also became deenergized to stop the normal sequencing of cuffs 1 and 2.

Thus, the slow leak in cuff 2 had been handled properly, by causing cuff 1 to inflate, deflating cuff 2, and indicating a failure mode. The energization of lamp 44a and the corresponding deenergization of lamp 44b will indicate to the attendant that the problem lies with cuff 2 and not cuff 1.

A third failure mode can occur if a restriction occurs in the breathing passages of a patient. The continued operation of the respirator raises a danger of overpressurizing the patient. However, pressure sensing switch 26 will sense the pressure in tracheal tube 4 rising above some predetermined threshold and cause the switch 26a (in FIG. 4) to make contact 26c, instead of contact 26b. When this occurs, regardless of the positioning of the timer switches 27a and 27b, both solenoids will be energized. One will be energized from the power line through contacts 26c, switch 26d, and switch 33. When switch 26a moved to its lefthand position it opened the circuit for relay 34 and timer motor 27. When relay 34 becomes deenergized, power is supplied via the back contact at 34b to the other of solenoids 15 and 20. As both cuffs become deflated, pressure switches 22a and 24a close and thus both relays 30 and 31 become energized. Since both cuffs are deflated now, there is no danger of overpressurization as the endo-tracheal tube is no longer sealed off from the atmosphere. As the respirator moves through its normal cycle, the pressure it supplies endo-tracheal tube 4 will decrease, and when it decreases sufficiently so that switch 26a makes its righthand contact 26b, the energization path for solenoid 15 will be opened and thus this solenoid will become deenergized allowing cuff 1 to inflate. Note that the relay 34 and the timer motor 27 are deenergized; therefore, the the contacts 27a, 27b and 27c will no longer change their position with time and the red warning indicator 42 and audible alarm 35 are energized. As the respirator goes through its cycle, switch 26a will flip back and forth between contacts 26b and 26c. When in the lefthand position in response to a high pressure condition, both cuffs will be deflated to protect the patient. When switch 26a is in its righthand position, cuff 1 will be inflated providing a seal for the respirator system. However, during this entire period of time, the red warning light 42 and the audible alarm 35 are energized to indicate a failure condition. They system will maintain this state until reset switch 28 is closed to resume normal operation.

From the foregoing description of the pneumatic and electrical control system, the operation of the cuffs should be apparent. Referring to FIG. 1, we will assume that cuff 1 is inflated and cuff 2 is deflated. During this time, as the respirator increases and decreases the pressure in tracheal tube 4, the pressure in cuff 1 will change in a like manner. Reference to FIG. 3 shows that as the pressure in tracheal tube 4 increases, the expansion of bellows 13 causes a corresponding contraction of bellows 12 to correspondingly increase the pressure in the cuff 1. Similarly, as the pressure in the endo-tracheal tube 4 decreases, the contraction of bellows unit 13, responsive thereto, allows bellows unit 12 to expand, thus also decreasing the pressure in cuff 1. After cuff 1 has operated in this manner for a predetermined period of time, (20 minutes has been suggested) the electrical control system will cause cuff 2 to become inflated, as well. After a short period of time, such as 30 seconds, during which time both cuffs are inflated, cuff 1 will be deflated. Thereafter, cuff 2 will operate in the same manner as cuff 1 had operated until the control system again causes cuff 1 to be inflated.

Thus, an alternating cuff endo-tracheal tube has been provided in which the cuffs are automatically controlled. Furthermore, the system is fail-safe, in that an electrical failure or a rupture in one or the other of the cuffs will not result in any danger to the patient. In case of an electrical failure, both cuffs become inflated and the control system signals the attendant. If one or the other of the cuffs ruptures, the other cuff becomes inflated and again the control system signals an attendant. In addition, as has been explained, the system prevents overpressurization be deflating the seal when the pressure in the tracheal tube 4 exceeds a predetermined threshold which corresponds to overpressurization. Furthermore, the seal is only deflated during the period of time when overpressurization may occur. That is, as the respirator goes through its cycle, the seal will only be deflated during that portion of the cycle where overpressurization of the patient may occur.

The automatic multi-cuff endo-tracheal tube disclosed above has been tested, to date, on four patients for a total of 271 hours of operation. During this time, the unit performed flawlessly. The table below shows the number of hours used for each of the patients involved.

| Patient | Hours of Use |
|---------|--------------|
| I | 13 |
| II | 47 |
| III | 188 |
| IV | 23 |

The embodiment of the device utilized with respect to patients I and III developed leaks. However, these leaks were safely and properly handled by the control system. On the first patient, the two cuffs developed a leak so that when cuff number 1 was inflated, air would leak into cuff number 2 and vice versa. This problem was solved by deenergizing the control unit, causing both cuffs to become inflated.

The third patient's number 2 cuff developed a leak (on the third day of operation) where it was bonded to the endo-tracheal tube. The automatic alternating cuff endo-tracheal tube corrected this problem and maintained an endo-tracheal seal by keeping cuff number 1 inflated.

As a result of the possibility of leaks, such as occurred in testing the apparatus referred to above, the control system must be designed to respond to such situations without endangering the patient. The manner in which the tested apparatus responded shows that the instant invention meets this requirement.

What I claim is:

1. An alternating cuff endo-tracheal tube including, an endo-tracheal tube,
at least two cuffs surrounding said endo-tracheal tube,
each of said cuffs capable of forming an air tight seal against the trachea when inflated, and
a control unit sensing pressure in each of said cuffs and in said endo-tracheal tube and controlling the pressure in both said cuffs, said control unit including, for each of said cuffs,
a moveable member urged in one direction to pressurize the associated cuff,
means responsive to pressurization of said endo-tracheal tube to further urge said moveable member in said one direction to increase pressure in said associated cuff,
and deflating means, when energized, to urge said moveable member in said other direction to deflate said associate cuff, and
timing means, when activated to energize and deenergize both said deflating means alternately and in sequence.

2. A pressure controlling device for controlling the pressure of a cuff on an endo-tracheal tube in accordance with pressure variations in said tube comprising,
a movable member normally urged in one direction,
first transducing means connected to said cuff and to said movable member to pressurize said cuff in response to movement in said one direction by said movable member,
and second transducing means connected to said tube and to said movable member to move said movable member in said one direction in response to pressure increases in said tube to thereby increase the pressure in said cuff and, to move said movable member in said other direction in response to pressure decreases in said tube to thereby decrease the pressure in said cuff.

3. The apparatus of claim 1 wherein said control means further includes,
means responsive to the pressure in a cuff being below a predetermined value when said associated deflating means is deenergized to deactivate said timing means to to deenergize the deflating means associated with said other cuff.

4. The apparatus of claim 3 which further includes a pressure responsive device sensing pressure in said tube,
said pressure responsive device causing energization of both said deflating means in response to pressure in said tube above a predetermined amount.

5. The apparatus of claim 3 which further includes means responsive to movement of said movable member in said one direction beyond a predetermined point to deactivate said timing means and to energize the deflating means associated with the cuff associated with said movable member and to deenergize the other deflating means.

6. A cuff inflating device for an endo-tracheal tube having a cuff, operated by a respirator supplying said tube, comprising
a movable member normally urged in one direction,
first transducing means connected to said cuff and to said movable member to pressurize said cuff in response to movement of said movable member in said one direction,
and second transducing means connected to said tube and to said movable member to urge said movable member in said one direction in response to increases in pressure in said tube.

7. The device of claim 6 which further includes deflating means to move said movable member in said other direction to deflate said cuff, when said deflating means is energized.

8. The device of claim 5 which further includes a unidirectional valve to admit air into said first transducing means but to prevent air from escaping from said transducing means.

9. The apparatus of claim 2 in which said moveable member includes a lever arm pivoted about a fulcrum.

10. The apparatus of claim 2 in which said first and second transducers comprise first and second bellows.

11. The apparatus of claim 2 in which a weight is supported by said moveable member to normally urge said moveable member in said one direction.

* * * * *